United States Patent
Wang et al.

(10) Patent No.: US 11,291,736 B2
(45) Date of Patent: Apr. 5, 2022

(54) PH-RESPONSIVE ULTRASENSITIVE FLUORESCENT NANOPROBE, PREPARATION AND USING METHOD THEREOF

(71) Applicant: Xidian University, XI'an (CN)

(72) Inventors: Zhongliang Wang, Xi'an (CN); Yongdong Wang, Xi'an (CN); Ruili Zhang, Xi'an (CN); Qian Jia, Xi'an (CN); Chaoqiang Qiao, Xi'an (CN); Jie Tian, Xi'an (CN)

(73) Assignee: XIDIAN UNIVERSITY, Xi'an (CN)

(*) Notice: Subject to any disclaimer, the term of this patent is extended or adjusted under 35 U.S.C. 154(b) by 469 days.

(21) Appl. No.: 16/074,778

(22) PCT Filed: Nov. 15, 2017

(86) PCT No.: PCT/CN2017/111139
§ 371 (c)(1),
(2) Date: Aug. 2, 2018

(87) PCT Pub. No.: WO2019/033594
PCT Pub. Date: Feb. 21, 2019

(65) Prior Publication Data
US 2020/0164092 A1    May 28, 2020

(30) Foreign Application Priority Data
Aug. 16, 2017 (CN) .......................... 201710703148.5

(51) Int. Cl.
*A61K 49/00* (2006.01)
(52) U.S. Cl.
CPC ...... *A61K 49/0054* (2013.01); *A61K 49/0032* (2013.01); *A61K 49/0034* (2013.01); *A61K 49/0041* (2013.01)
(58) Field of Classification Search
CPC ............ A61K 49/0034; A61K 49/0093; A61K 49/0032; A61K 49/0041; A61K 49/0054
See application file for complete search history.

(56) References Cited

U.S. PATENT DOCUMENTS

2007/0297988 A1* 12/2007 Wu ..................... A61K 49/0093
424/9.6
2015/0056142 A1* 2/2015 Tao ....................... G01N 33/553
424/9.6
2017/0321280 A1* 11/2017 Vo-Dinh .............. C12Q 1/6816

FOREIGN PATENT DOCUMENTS

| CN | 101508429 A | 8/2009 |
| CN | 101721709 A | 6/2010 |
| CN | 102830104 A | 12/2012 |
| CN | 104587488 A | 5/2015 |
| CN | 105169400 A | 12/2015 |
| KR | 20130043718 A | 5/2013 |

OTHER PUBLICATIONS

Morgan, Nano Lett., 2008, 8(12), p. 4108-115. (Year: 2008).*
Kim et al., Soft Matter, 2015, 11, p. 4402-7. (Year: 2015).*
Lauth et al., Chem. Mater., 2016, 28, p. 3796-3803. (Year: 2016).*
Lin-Chen Ho, et al, "Sensitive pH probes of retro-self-quenching fluorescent nanoparticles", Journal of Materials Chemistry B, Mar. 15, 2013, p. 2425-2432, vol. 1, No. 18.
Perkin K.K., et al; "Fabrication of Hybrid Nanocapsules by Calcium Phosphate Mineralization of Shell Cross-Linked Polymer Micelles and Nanocages", Nano Letters, Jun. 22, 2005, p. 1457-1461, vol. 5, No. 7.

* cited by examiner

*Primary Examiner* — Michael G. Hartley
*Assistant Examiner* — Leah H Schlientz
(74) *Attorney, Agent, or Firm* — Bayramoglu Law Offices LLC

(57) ABSTRACT

The pH-responsive ultrasensitive fluorescent nanoprobe is composed of pH-responsive matrix materials and fluorescent organic small molecule dyes. The pH-responsive matrix materials are calcium phosphate, calcium hydroxyphosphate, fluorapatite, calcium carbonate or ZIF series; the fluorescent organic small molecule dyes are positively charged dyes or negatively charged dyes. The preparation method includes: coating a positively charged dye with a negatively charged matrix material; coating a negatively charged dye with a negatively charged matrix material; and coating a negatively charged dye with a positively charged matrix material. Compared with traditional small molecule fluorescent dyes, the present invention can greatly improve the sensitivity and specificity of fluorescence imaging and achieve ultrasensitive detection of tumor microenvironment response; the specific response probe prepared by the unique properties of the tumor microenvironment has the advantages of high targeting efficacy, low background signal, and high signal-to-noise ratio, and can achieve ultrasensitive detection of tiny tumors.

12 Claims, 7 Drawing Sheets

PH-RESPONSIVE ULTRASENSITIVE FLUORESCENT NANOPROBE, PREPARATION AND USING METHOD THEREOF

CROSS REFERENCE TO RELATED APPLICATIONS

This application is the national phase entry of International Application No. PCT/CN2017/111139, filed on Nov. 15, 2017, which is based upon and claims priority to Chinese Application No. CN2017107031485, filed on Aug. 16, 2017, the entire contents of which are incorporated herein by reference.

TECHNICAL FIELD

The present invention relates to the technical field of molecular imaging, and particularly to a pH-responsive ultrasensitive fluorescent nanoprobe, preparation and using method thereof.

BACKGROUND

Molecular imaging can be used to study the occurrence, development and metastasis of diseases or tumors in vivo because of its ability to realize real-time, non-invasive and dynamic imaging at the living body level. Optical imaging has the advantages of like no radiation, high sensitivity, and low light damage to biological tissues, showing great potential in the research field of in vivo tumor monitoring. Due to the rapid proliferation of cells, tumor tissue tends to cause rapid glucose metabolism, large oxygen consumption, and excessive accumulation of acidic metabolites (such as lactic acid) in the tumor microenvironment. Therefore, the tumor microenvironment is generally characterized by weak acidity, hypoxia, production of a plurality of cytokines and high expression of biological enzymes. Conventional organic small molecule fluorescent probes, because of the non-specific distribution in vivo, will cause organic dyes generally to have the disadvantages of poor bio-distribution specificity, high background signal, poor light stability and easy photobleaching, thus being limited in the application of in vivo imaging, and cannot be applied to the detection of tiny tumors. The use of bio-intelligent responsive nanomaterial-loaded small molecule fluorescent probes can not only improve the light stability of small molecule fluorescent probes, but also achieve the high-efficient and specific enrichment of probes and the pH regulated fluorescence enhancement in the tumor sites, which has become a popular research direction in the field of molecular imaging technology.

SUMMARY

In view of the problems existing in the prior art, the present invention provides a pH-responsive ultrasensitive fluorescent nanoprobe, preparation and using method thereof.

The present invention is achieved by a pH-responsive ultrasensitive fluorescent nanoprobe, the pH-responsive ultrasensitive fluorescent nanoprobe is composed of pH-responsive matrix materials and organic small molecule dyes having fluorescent;

the negatively charged pH-responsive matrix materials are calcium phosphate (abbreviated as CaP), calcium hydroxyphosphate, fluorapatite, and calcium carbonate.

Further, positively charged pH-responsive matrix materials are zeolite imidazole framework (ZIF) material series;

the fluorescent organic small molecule dyes are positively charged dyes or negatively charged dyes.

Further, the positively charged dyes are IR780, RhB, or IR800.

Further, the negatively charged dyes are Cy3, Cy5, Cy5.5, Cy7, ICG, ICG-Der-01, ICG-Der-02, ICG-Der-03, IR820, Alexa Fluor 750, Alexa Fluor 700, Alexa Fluor 680, Alexa Fluor 660, Alexa Fluor 647, Alexa Fluor 635, Alexa Fluor 633, Alexa Fluor 610, Alexa Fluor 594, Alexa Fluor 568, Alexa Fluor 555, Alexa Fluor 546, Alexa Fluor 532, Alexa Fluor 514, Alexa Fluor 500, Alexa Fluor 488, or FITC.

Another purpose of the present invention is to provide a method for preparing the pH-responsive ultrasensitive fluorescent nanoprobe, and the method for preparing the pH-responsive ultrasensitive fluorescent nanoprobe includes the following three methods.

The first method, a positively charged dye is coated with a negatively charged matrix material, the dye is adsorbed on the PAA (polyacrylic acid) molecular chain by electrostatic interaction between the polyacrylic acid and the positively charged dye, and the PAA after dye adsorption is self-assembled to form a template in isopropyl alcohol, while the fluorescence of the dye is quenched by aggregation; the exposed carboxyl on the PAA is coordinated with $Ca^{2+}$, and the calcium phosphate is deposited on the surface of the PAA sphere by adjusting the pH and adding phosphate for mineralization to form a dye-coated nanoparticle.

The second method, a negatively charged dye is coated with a negatively charged matrix material, the dye is enriched on the polyetherimide (PEI) molecular chain through the absorption of the negatively charged dye by PEI; meanwhile, a negatively charged PAA is added, the PEI absorbs both dye and PAA to self-assembled into a PEI/PAA nanospheres; the exposed carboxyl on the PAA is coordinated with $Ca^{2+}$, and the calcium phosphate is deposited on the surface of the PAA sphere by adjusting the pH and adding phosphate for mineralization to form a dye-coated nanoparticle.

The third method, a negatively charged dye is coated with a positively charged matrix material, the dye molecules are adsorbed on the ligand (methylimidazole) molecules by the mutual electrostatic adsorption between the methylimidazole and the coated dye, meanwhile, the aggregation of the dye is caused, and the metal ions are added for being coordinated with the ligand to form a stable three-dimensional structure, thus forming a dye-coated nanoparticle.

Further, in the first method, the negatively charged pH-responsive matrix materials are calcium phosphate, calcium carbonate, calcium hydroxyphosphate, and fluorapatite; the positively charged dyes are IR780, RhB, or IR800.

Further, in the second method, the negatively charged pH-responsive matrix materials are calcium phosphate, calcium carbonate, calcium hydroxyphosphate, and fluorapatite; the negatively charged dyes are ICG, IR820, Alexa Fluor series dyes, and Cy series dyes.

Further, in the third method, the pH-responsive matrix materials are the MOF materials of the ZIF series; the negatively charged dyes are ICG, IR820, Alexa Fluor series dyes, and Cy series dyes.

Another purpose of the present invention is to provide a method for using the pH-responsive ultrasensitive fluorescent nanoprobe, and the method for using the pH-responsive ultrasensitive fluorescent nanoprobe includes: The nanoparticle is injected into the mouse via tail vein, which reaches the tumor site through the enhanced permeability and retention (EPR) effect and is enriched in the tumor site.

In normal tissues and blood, the pH is neutral or weakly alkaline, and the fluorescent molecules in the nanoparticles are in the state of aggregation quenching. In the tumor site, due to its weak acidic conditions, the matrix material CaP is dissolved and releases the fluorescent molecules, and the fluorescent recovers after the IR780 recovers to the free molecular state, thereby realizing fluorescence enhancement.

Another purpose of the present invention is to provide a CaP/IR780 probe and a CaCO$_3$/RhB probe prepared by the pH-responsive ultrasensitive fluorescent nanoprobe.

Another purpose of the present invention is to provide a CaP/ICG probe and a CaCO$_3$/Cy5 probe prepared by the pH-responsive ultrasensitive fluorescent nanoprobe.

Another purpose of the present invention is to provide a ZIF-8/ICG probe prepared by the pH-responsive ultrasensitive fluorescent nanoprobe.

The advantages and positive effects of the present invention are: the high-efficiency specificity enrichment and controllable release of the small molecule fluorescent probe at the tumor site can be achieved through the response of matrix materials to the weakly acidic conditions of the tumor microenvironment, the fluorescence intensity of the probe after release is significantly enhanced, and the ultrasensitive detections of the primary lesions and metastatic lesions of tumors are realized; matrix nanomaterials have pH response characteristic, under neutral conditions, fluorescent molecules loaded in nanoparticles are subjected to fluorescence quenching due to being in aggregation state; under the weakly acidic conditions of the tumor microenvironment, the matrix material is dissolved, so that the fluorescent molecules loaded in the nanoparticles recover to the single molecule state, the fluorescence is recovered, the tumor microenvironment acidic-responsive fluorescence enhancement is realized, and accurate imaging and real-time monitoring of early tumors can be realized.

The present invention can realize the high-efficiency enrichment of nanomaterials at the tumor site through the enhanced permeability and retention (EPR) effect of the nanomaterial at the tumor site, and the tumor-specific fluorescence enhancement can be achieved by utilizing the characteristic of pH response to the tumor microenvironment. Before reaching the tumor site, fluorescence quenching of fluorescent molecules in the probe was caused by the aggregation of the fluorescent molecules loaded in the matrix material, and the fluorescent signal was in a closed (OFF) state; while the probe is in a weakly acidic condition of the tumor microenvironment, the organic fluorescent molecules are released from the matrix material to achieve a pH-responsive "deaggregation" to enable the fluorescent signal recovery (ON). The OFF-ON switch minimizes the background signal of the fluorescent probe and significantly increases the imaging signal-to-noise ratio by nearly three times. Compared with the traditional small molecule fluorescent dyes, the sensitivity and specificity of fluorescence imaging can be greatly improved, and ultrasensitive detection of tumor microenvironment response can be realized; the specificity response probe prepared by the unique properties of the tumor microenvironment has the advantages of high targeting efficacy, low background signal, and high signal-to-noise ratio, and the ultrasensitive detection of tiny tumors smaller than 1 mm can be realized in vivo.

DETAILED DESCRIPTION OF THE EMBODIMENTS

In order to make the purpose, technical scheme and advantages of the present invention more clear, the present invention will be further described in detail below with reference to the embodiments. It should be understood that, the specific embodiments described herein are merely intended to explain the present invention rather than limit the present invention.

The principle of the present invention will be described in detail below with reference to the accompanying drawings.

The pH-responsive ultrasensitive fluorescent nanoprobes provided by the embodiments of the present invention are composed of pH-responsive matrix materials and fluorescent organic small molecule dyes.

The pH-responsive matrix material has a fast response to pH, and the pH-responsive dye molecules are released by the response of the pH-responsive matrix material to weakly acidic conditions. The main selection of the pH-responsive matrix material can be as follows: calcium phosphate, calcium hydroxyphosphate, fluorapatite, and calcium carbonate, ZIF series etc.; the matrix materials have the advantages of good biocompatibility, fast pH response, and safe and non-toxic metabolites.

Fluorescence organic small molecule dyes are the source of fluorescence signal, and the quenching/recovering transformation of the fluorescence is realized by the pH-responsive aggregation and deaggregation to achieve the pH-responsive fluorescence enhancement (OFF-ON). Organic fluorescent small molecules are dye molecules with aggregation quenching effect, the organic fluorescent small molecules can be: positively charged dyes such as IR780, RhB, IR800, etc., or negatively charged dyes such as Cy3, Cy5, Cy5.5, Cy7, ICG, ICG-Der-01, ICG-Der-02, ICG-Der-03, IR820, Alexa Fluor 750, Alexa Fluor 700, Alexa Fluor 680, Alexa Fluor 660, Alexa Fluor 647, Alexa Fluor 635, Alexa Fluor 633, Alexa Fluor 610, Alexa Fluor 594, Alexa Fluor 568, Alexa Fluor 555, Alexa Fluor 546, Alexa Fluor 532, Alexa Fluor 514, Alexa Fluor 500, Alexa Fluor 488, FITC, etc. Fluorescent organic small molecule dyes have the advantages of long emission wavelength, weaker light scattering signal in vivo, deep detection depth and good alkali stability.

Figure 1:
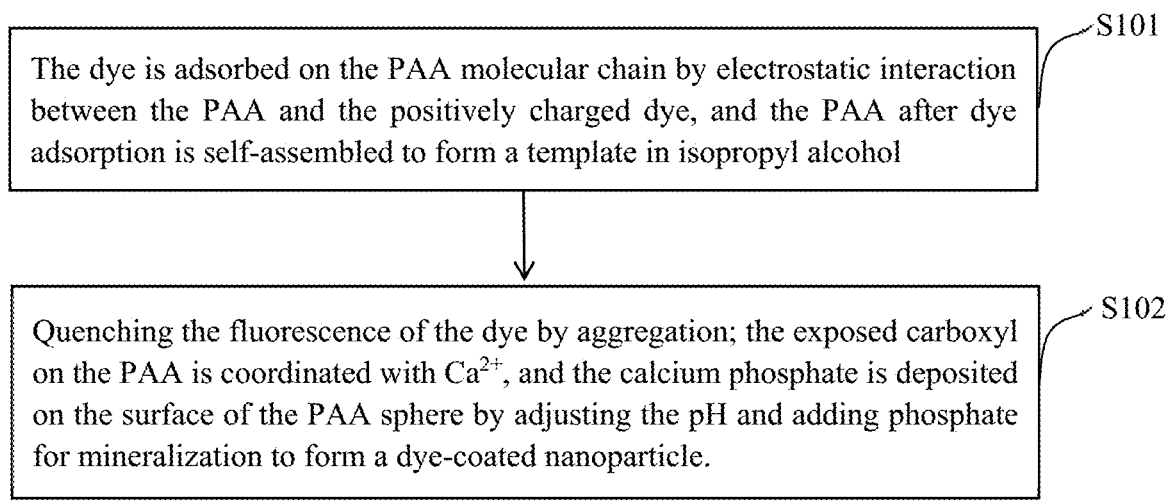
FIG. 1 is a flow chart of preparation method of a pH-responsive ultrasensitive fluorescent nanoprobe provided by embodiments of the present invention.

As shown in FIG. 1, a preparation method of a pH-responsive ultrasensitive fluorescent nanoprobe provided by an embodiment of the present invention includes the following steps:

S101: the dye is adsorbed on the PAA molecular chain by electrostatic interaction between the PAA and the positively charged dye, and the PAA after dye adsorption is self-assembled to form a template in isopropyl alcohol;

S102: quenching the fluorescence of the dye by aggregation; the exposed carboxyl on the PAA is coordinated with $Ca^{2+}$, and the calcium phosphate is deposited on the surface of the PAA sphere by adjusting the pH and adding phosphate for mineralization to form a dye-coated nanoparticle.

The negatively charged matrix materials can be calcium phosphate, calcium carbonate, calcium hydroxyphosphate, fluorapatite, etc., the positively charged dyes used in the embodiment can be IR780, RhB, IR800, etc. The synthetic probes include CaP/IR780, $CaCO_3$/RhB, etc.

The preparation method of the pH-responsive ultrasensitive fluorescent nanoprobe provided by the embodiment of the present invention also includes: a negatively charged dye is coated with a negatively charged matrix material, and the dye is enriched on the PEI molecular chain due to the absorption of the negatively charged dye by PEI; meanwhile, a negatively charged PAA is added, and then the PEI absorbs both dye and PAA and is self-assembled into a PEI/PAA nanospheres; the exposed carboxyl on the PAA is coordinated with $Ca^{2+}$, and the calcium phosphate is deposited on the surface of the PAA sphere by adjusting the pH and adding phosphate for mineralization to form a dye-coated nanoparticle.

The negatively charged matrix materials can be calcium phosphate, calcium carbonate, calcium hydroxyphosphate, fluorapatite, etc., the negatively charged dyes used in the embodiment can be ICCG, IR820, Alexa Fluor series dyes, and Cy series dyes. Probes synthesized by this method include CaP/ICCG, $CaCO_3$/Cy5, etc.

The preparation method of the pH-responsive ultrasensitive fluorescent nanoprobe provided by the embodiment of the present invention also includes: a negatively charged dye is coated with a positively charged matrix material, the dye molecules are adsorbed on the ligand (methylimidazole) molecules by the mutual electrostatic adsorption between the ligand and the coated dye, meanwhile, the aggregation of the dye is caused, and the metal ions are added for coordinating with the ligand to form a stable three-dimensional structure, then forming a dye-coated nanoparticle.

The positively charged matrix materials can be MOF materials of the ZIF series, such as ZIF-8, etc., the negatively charged dyes used in the embodiment can be ICG, IR820, Alexa Fluor series dyes, and Cy series dyes. Probes synthesized by this method include ZIF-8/ICG, etc.

The specific operating method of the probe prepared by the present invention for tumor imaging in vivo is:

The nanoparticle is injected into the mouse via tail vein, which reaches the tumor site through the EPR effect and is enriched in the tumor site. In normal tissues and blood, the pH is neutral (or weakly alkaline), and the fluorescent molecules in the nanoparticles are in the state of aggregation quenching. In the tumor site, due to its weak acidic conditions, the matrix material CaP is dissolved and releases the fluorescent molecules, and the fluorescent recovers after the IR780 recovers to the free molecular state, therefore, fluorescence enhancement is realized, and the pH-responsive fluorescence enhancement is realized in the whole imaging process.

The application principle of the present invention will be further described below with reference to the specific embodiments.

Embodiment 1

Preparation of CaP/IR780 Nanoprobe

Synthesis principle: the dye is aggregated by electrostatic interaction between the PAA and IR780 to achieve fluorescence quenching, the PAA after dye adsorption is self-assembled to form a template in isopropyl alcohol, and the calcium phosphate is deposited on the surface of the PAA sphere by mineralization to form a CaP/IR780 nanoparticle.

Figure 2:
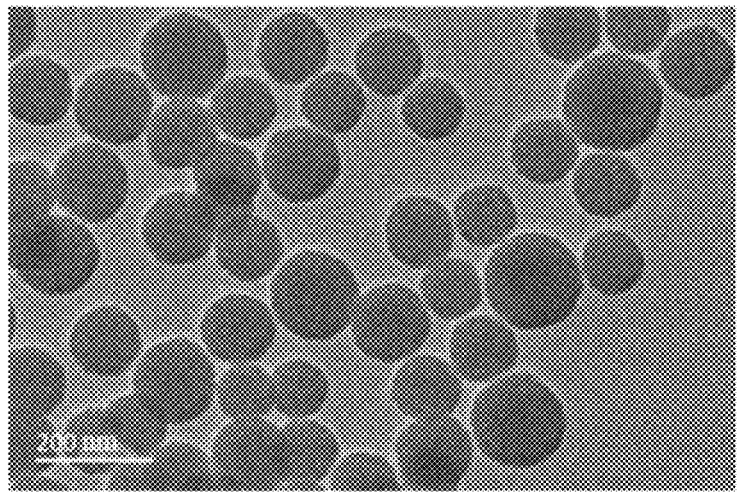
FIG. 2 is a TEM diagram of CaP/IR780-PEG provided by an embodiment of the present invention.
Figure 3:
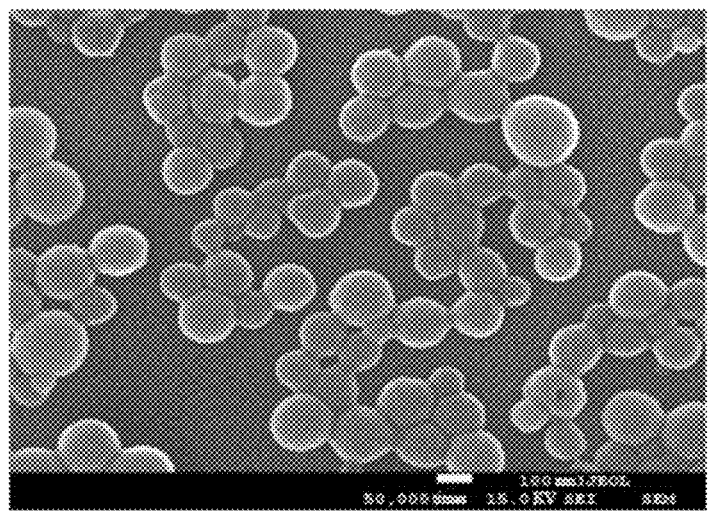
FIG. 3 is a SEM diagram of CaP/IR780-PEG provided by an embodiment of the present invention.
Figure 4:
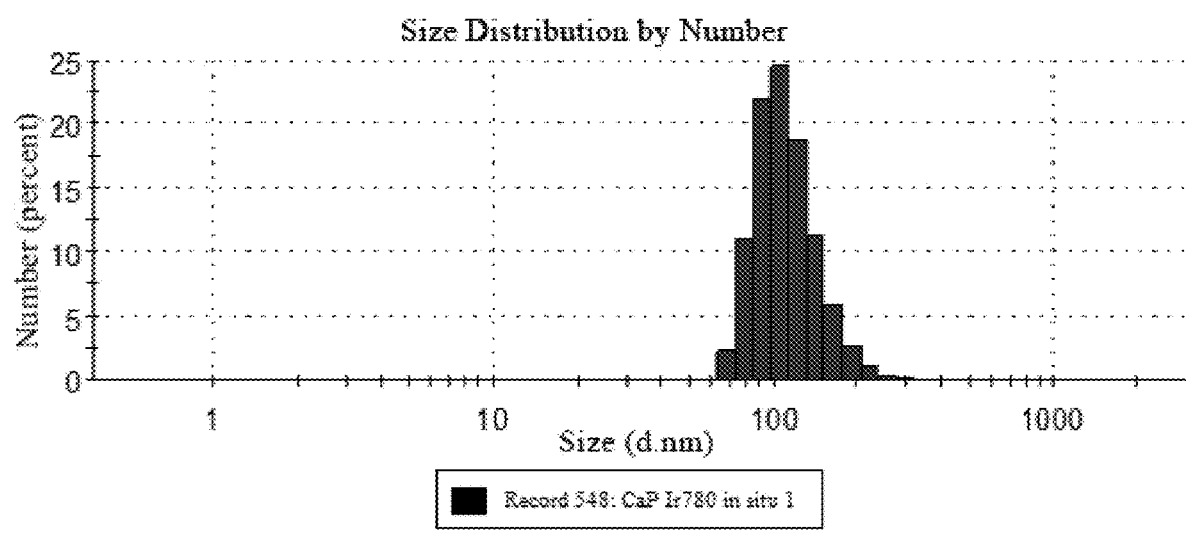
FIG. 4 is a DLS diagram of CaP/IR780-PEG provided by an embodiment of the present invention.
Figure 5:
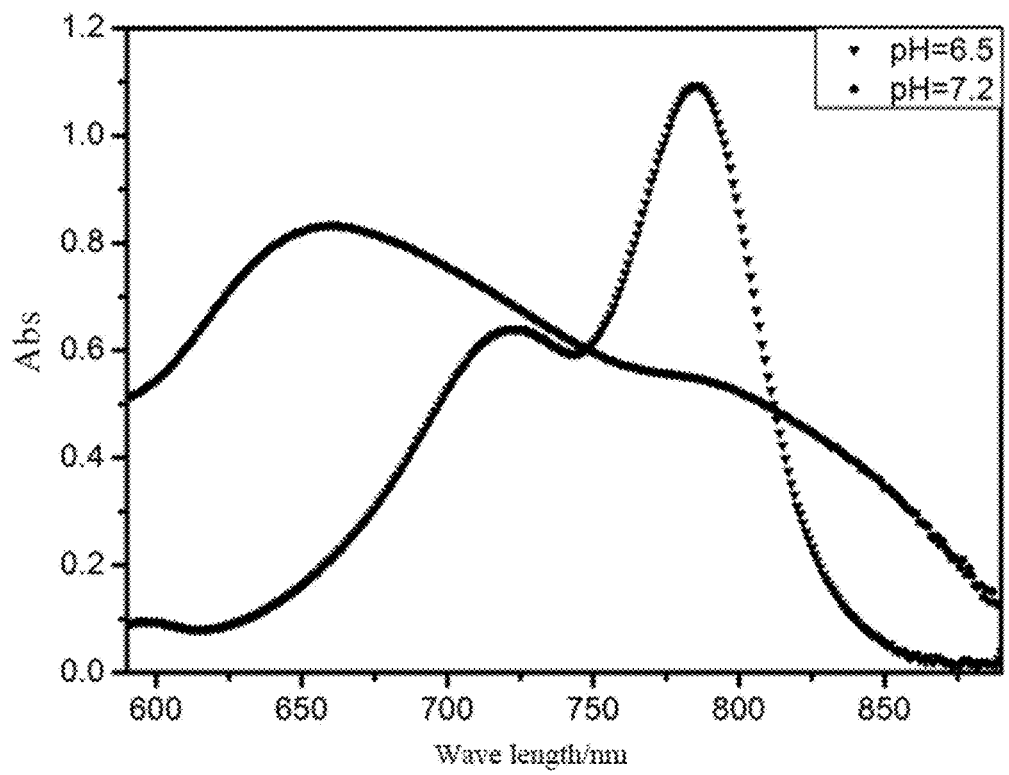
FIG. 5 is a ultraviolet-visible spectroscopy showing pH-responsive characteristic of CaP/IR780 provided by an embodiment of the present invention.
Figure 6:
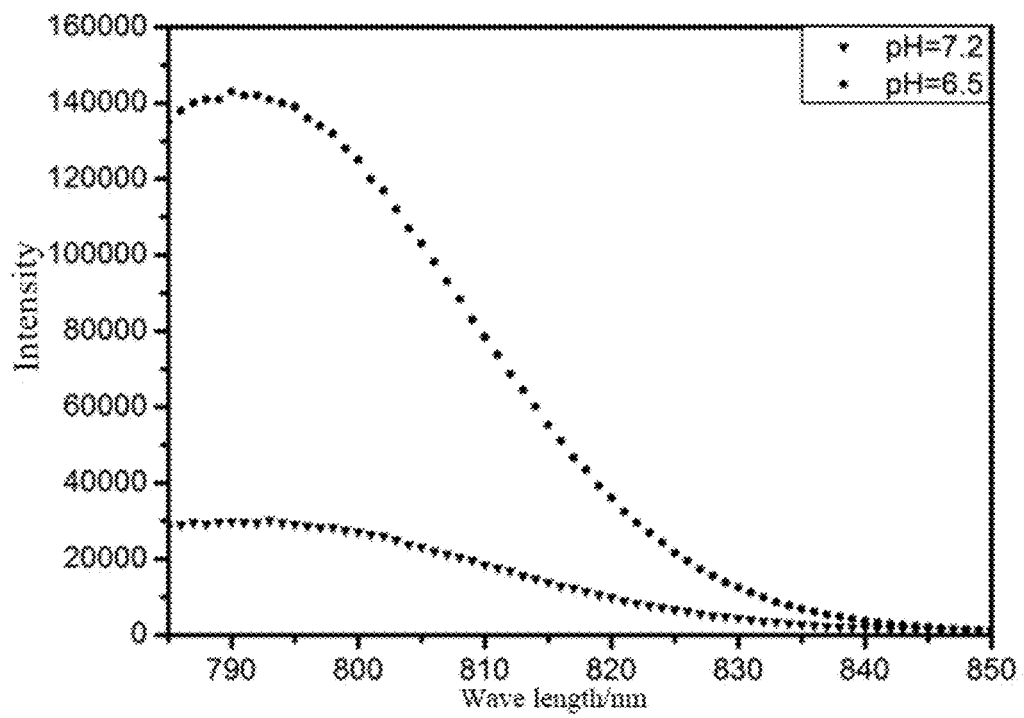
FIG. 6 is a fluorescence spectrum showing pH-responsive characteristic of CaP/IR780 provided by an embodiment of the present invention.

Specific synthesis steps: dissolving 60-80 µL 20% PAA (MW=2000) in 10 mL water, adding 5-8 mg $Ca(OH)_2$, stirring to dissolve, adding 50-1000 µg IR780, stirring for 30 min for mixing well. Slowly adding 10-50 mL of isopropanol to form a milky white solution, adding 6-9.6 mg $(NH_4)_2HPO_4$ and stirring for 24 h, centrifuging, and washing for 3 times, redistributing in 5 mL water for standby application. Characterizations of particle size were performed by the transmission electron microscopy (TEM), the scanning electron microscopy (SEM) and the dynamic light scattering (DLS) as shown in FIG. 2, FIG. 3 and FIG. 4; the ultraviolet-visible spectroscopy of the nanoparticles with different dyes coated were measured by the ultraviolet-visible spectrophotometer, respectively, as shown in FIG. 5; the ultraviolet-visible spectroscopy of the nanoparticles with different dyes coated were measured at the pH of 6.5, as shown in FIG. 6. In order to improve the stability of the nanoprobe and the circulation time in the blood of the animals, the surface of the probe is stabilized by PEG, thus improving the stability of the probe. Adding 10 mg of 1-(3-Dimethylaminopropyl)-3-ethylcarbodiimide (EDC), 12 mg of N-Hydroxysuccinimide (NHS) and 5 mg of polyethylene glycol amine (PEG-$NH_2$) to the above particle dispersion system, adjusting pH to 7.2, stirring at room temperature for 24 h, centrifuging, washing for 3 times with water, and dispersing in 5 mL of phosphate-buffered saline (PBS) for standby application.

Embodiment 2

Preparation of CaP/RhB Nanoprobe

Synthesis principle: the dye is aggregated by electrostatic interaction between the PAA and RhB to achieve fluorescence quenching, the PAA after dye adsorption is self-assembled to form a template in isopropyl alcohol, and the calcium phosphate is deposited on the surface of the PAA sphere by mineralization to form a CaP/RhB nanoparticle.

Specific synthesis steps: dissolving 60-90 µL 20% PAA (MW=4500) in 10 mL water, adding 5-10 mg $Ca(OH)_2$, stirring to dissolve, adding 100-1000 µg RhB, stirring for 30 min for mixing well. Slowly adding 30 mL of isopropanol to form a milky white solution, adding 6.2-12 mg $(NH_4)_2HPO_4$ and stirring for 24 h, centrifuging, and washing for 3 times, redistributing in 5 mL water. In order to improve the stability of the nanoprobe and the circulation time in the blood of the animals, the surface of the probe is stabilized by PEG, thus improving the stability of the probe. Adding 5 mg of PEG-COOH to the above particle dispersion system, adjusting pH to 7.2, stirring at room temperature for 24 hours, centrifuging, washing for 3 times with water, and dispersing in 5 mL of PBS for standby application.

Embodiment 3

Preparation of $CaCO_3$/ICG Nanoprobe

Synthesis principle: the dye is enriched on the PEI molecular chain due to the absorption of the ICG by PEI, and the calcium carbonate is deposited on the surface of the PAA sphere by adjusting the pH and adding carbonate for mineralization to form a ICG-coated $CaCO_3$ nanoparticle.

Specific synthesis steps: adding 20-100 µL 0.1M $CaCl_2$ to 10 mL 10-50 µg·mL$^{-1}$ ICG solution including 0.2-1 mg PEI, stirring evenly, adding 25-75 µL 0.1M $NaHCO_3$, reacting at 70° C. for 2 h, centrifuging and dispersing in deionized water. Adding 5 mg HOOC-$PEG_{5K}$, adjusting pH to 7.2, stirring overnight, centrifuging, and redispersing in 5 mL of PBS for standby application.

Embodiment 4

Preparation of CaP/ICG Nanoprobe

Synthesis principle: the dye is enriched on the PEI molecular chain due to the absorption of the ICG by PEI, meanwhile, a negatively charged PAA is added, and then the PEI absorbs both dye and PAA and is self-assembled into a PEI/PAA nanospheres, the exposed carboxyl on the PAA is coordinated with $Ca^{2+}$, and the calcium phosphate is deposited on the surface of the PAA sphere by adjusting the pH and adding phosphate for mineralization to form a ICG-coated CaP nanoparticle.

Specific synthesis steps: dissolving 50-70 µL 20% PAA (MW=2000) in 10 mL water, adding 5-10 mg $Ca(OH)_2$, stirring to dissolve, dissolving 0.05-1 mg ICG to 0.2-1 mL 0.2 mg·mL$^{-1}$ PEI solution, shaking for 0.5 h, slowly dropwise adding to the above solution, stirring for 10 min, slowly adding 30 mL of isopropanol to form a milky white solution, adding 6.2-10 mg $(NH_4)_2HPO_4$ and stirring for 24 h, centrifuging, and washing for 3 times, dispersing in 5 mL water. In order to improve the stability of the nanoprobe and the circulation time in the blood of the animals, the surface of the probe is stabilized by PEG, thus improving the stability of the probe. Adding 10 mg of EDC, 12 mg of NHS and 5 mg of PEG-$NH_2$ to the above particle dispersion system, adjusting pH to 7.2, stirring at room temperature for 24 hours, centrifuging, washing for 3 times with water, and dispersing in 5 mL of PBS for standby application.

Embodiment 5

Preparation of $CaCO_3$/IR808 Nanoprobe

Synthesis principle: the dye is enriched on the PEI molecular chain due to the absorption of the IR808 by PEI, and the calcium carbonate is deposited on the surface of the PAA sphere by adjusting the pH and adding carbonate for mineralization to form a IR808-coated $CaCO_3$ nanoparticle.

Specific synthesis steps: adding 5-20 mg $CaCl_2$ and 0.2-2 mg PEI to 10 mL 50-1000 µg·mL$^{-1}$ IR808 solution, performing ultrasonic dispersion, and adding 0.2-1 ml 0.1 M $NaHCO_3$ with vigorous stirring, reacting for 12 h at 25° C., centrifuging and dispersing in 5 mL deionized water. In order to improve the stability of the nanoprobe and the circulation time in the blood of the animals, the surface of the probe is stabilized by PEG, thus improving the stability of the probe. Adding 5 mg $PO_4$-$PEG_{5K}$ to the above particle dispersion system, adjusting pH to 7.2, stirring at room temperature for 24 hours, centrifuging, washing for 3 times with water, and dispersing in 5 mL of PBS for standby application.

Embodiment 6

Preparation of CaP/IR820 Nanoprobe

Synthesis principle: the dye is enriched on the PEI molecular chain due to the absorption of the IR808 by PEI, meanwhile, a negatively charged PAA is added, and then the PEI absorbs both dye and PAA and is self-assembled into a PEI/PAA nanosphere, the exposed carboxyl on the PAA is coordinated with $Ca^{2+}$, and the calcium phosphate is deposited on the surface of the PAA sphere by adjusting the pH and adding phosphate for mineralization to form a IR820-coated CaP nanoparticle.

Specific synthesis steps: dissolving 50-70 µL 20% PAA (MW=2000) in 10 mL water, adding 5-10 mg $Ca(OH)_2$, stirring to dissolve, dissolving 0.05-1 mg IR820 to 0.2-1 mL 0.2 mg·mL$^{-1}$ PEI solution, shaking for 0.5 h, slowly dropwise adding to the above solution, stirring for 10 min, slowly adding 30 mL of isopropanol to form a milky white solution, adding 6.2-10 mg $(NH_4)_2HPO_4$ and stirring for 24 h, centrifuging, and washing for 3 times with water, dispersing in 5 mL water.

Embodiment 7

Preparation of ZIF-8/ICG Nanoprobe

Synthesis principle: the dye molecules are adsorbed on the ligand (methylimidazole) molecules by the mutual electrostatic adsorption between the methylimidazole and the ICG, meanwhile, the aggregation of the dye is caused, and the zinc ion was added for being coordinated with the ligand to form a stable three-dimensional structure, then forming a dye-coated nanoparticle.

Figure 7:
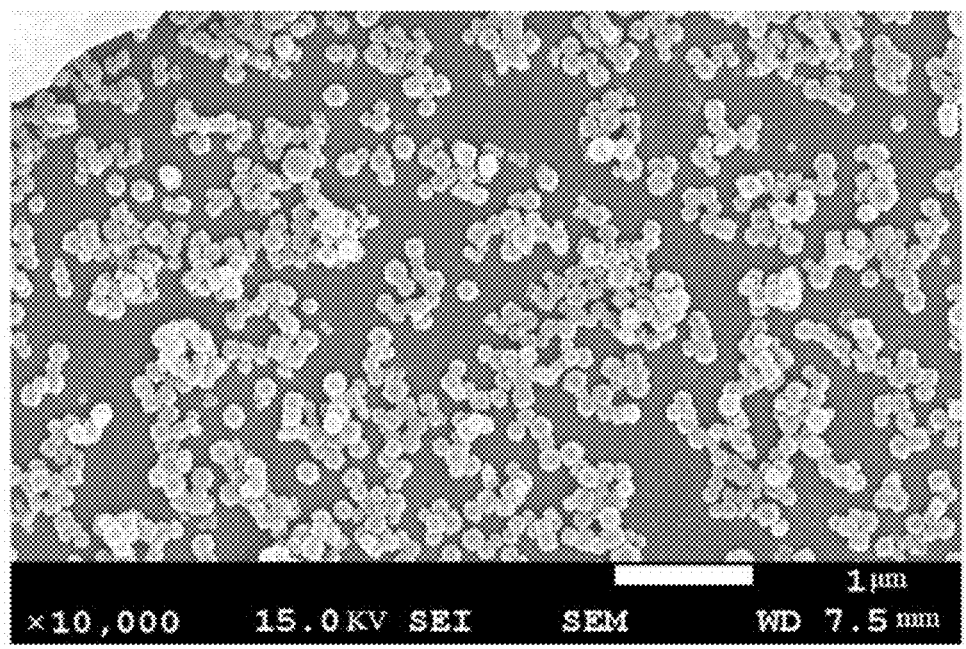
FIG. 7 is a SEM diagram of ZIF8/ICG provided by an embodiment of the present invention.

Specific synthesis steps: dissolving 1 mmol of $Zn(NO_3)_2$ and 1 mmol of 2-methylimidazole in 10 mL of methanol, and adding 5-300 µL of glacial acetic acid, ultrasound for 30 minutes, centrifuging and dispersing in methanol to obtain a solution. The particle size was determined by scanning electron microscopy as shown in FIG. 7. Adding 100 µL of 1 mg·mL$^{-1}$ ICG methanol solution to the above solution, shaking overnight, centrifuging, and dispersing in 5 mL of methanol. Adding 5 mg of mPEG-COOH for shaking overnight, centrifuging, and dispersing in 5 mL of PBS for standby application.

Embodiment 8

Preparation of ZIF-8/Cy5.5 Nanoprobe

Synthesis principle: the dye molecules are adsorbed on the ligand (methylimidazole) molecules by the mutual electrostatic adsorption between the methylimidazole and the Cy5.5, meanwhile, the aggregation of the dye is caused, and the zinc ion was added for being coordinated with the ligand to form a stable three-dimensional structure, then forming a dye-coated nanoparticle.

Specific synthesis steps: dissolving 1 mmol of $Zn(CH_3COO)_2$ and 1 mmol of 2-methylimidazole in 10 mL of methanol, and adding 5-300 µL of glacial acetic acid, ultrasound for 30 minutes, centrifuging and dispersing in methanol to obtain a solution. Adding 100 µL of 0.5 mg·mL$^{-1}$ Cy5.5 methanol solution to the above solution, shaking overnight, centrifuging, and dispersing in 5 mL of methanol. Adding 5 mg of mPEG-COOH for shaking overnight, centrifuging, and dispersing in 5 mL of PBS for standby application.

The application effects of the present invention will be described in detail below with reference to experiments.

1. Stability Test of Nanoprobe In Vitro

Figure 8:
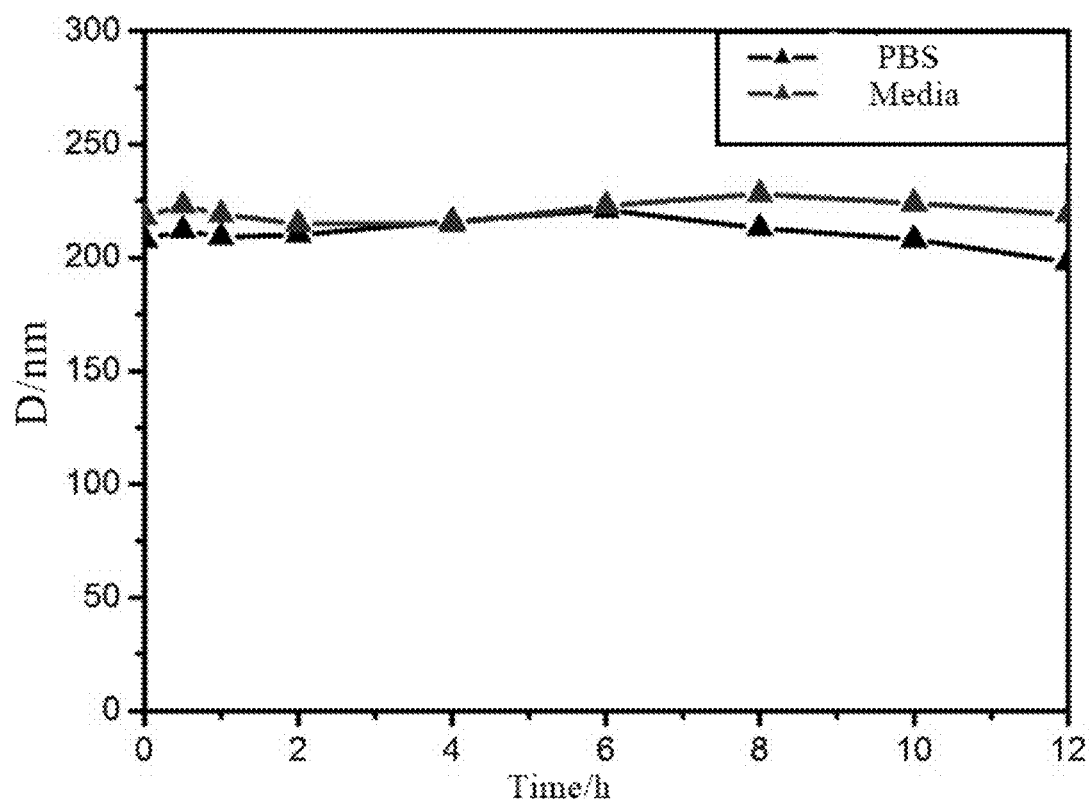
FIG. 8 is a graph showing stability curves of CaP/IR780 in different media provided by an experiment of the present invention.

Dispersing the prepared nanoprobes in PBS and FBS, respectively, and monitoring the changes of the sizes of the nanoprobes at 0 h, 1 h, 2 h, 4 h, 8 h, and 12 h by DLS, as shown in FIG. 8. Dispersing the prepared nanoprobe in FBS and centrifuging at 0 h, 1 h, 2 h, 4 h, 8 h, 12 h, 24 h, respectively; obtaining the UV-vis spectroscopy of the supernatant, respectively; the absorption intensity of the dye in the supernatant was quantitatively measured at the maximum absorption wavelength, the stability of the dyes in the nanoparticles were determined by measuring the absorption intensity, as shown in FIG. 8.

2. pH Responsive Experiment of Nanoparticles In Vitro

Dispersing the prepared nanoparticles in PBS at pH of 7.2, 6.8 and 6.0, respectively; obtaining the fluorescence spectrum of the solution, and the fluorescence intensity was quantitatively measured at the fluorescence emission wavelength, the pH response characteristics of the nanoparticles were determined by quantitatively measuring the change of fluorescence intensity.

3. Cytotoxicity Experiment of Nanoparticles

Figure 9:
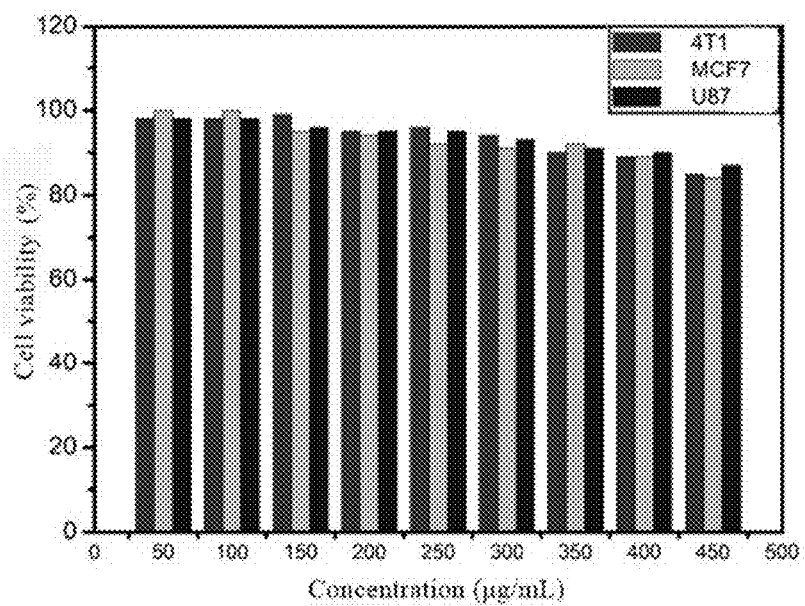
FIG. 9 is a schematic diagram of cytotoxicity experiment of a nanoprobe provided by an experiment of the present invention.

Discarding the medium of the U87, MCF-7 and 4T1 cells in exponential growth phase, washing the cells with PBS, digesting with 0.25% trypsin containing 0.02% EDTA, centrifuging and collecting the cells; adding the prepared cell culture medium to prepare a cell suspension with a cell concentration of about $5 \times 10^4$ cells·mL$^{-1}$, adding 100 μL cell suspension per well to a 96-well plate, placing it in the incubator for 12 h. Adding 100 μL of the probe solution with different concentrations (0 μg·mL$^{-1}$, 5 μg·mL$^{-1}$, 10 μg·mL$^{-1}$, 25 μg·mL$^{-1}$, 50 μg·mL$^{-1}$, 100 μg·mL$^{-1}$, 200 μg·mL$^{-1}$, 300 μg·mL$^{-1}$) to the 96-well plate, setting the control groups, and incubating with the cells for 12 h, 24 h, respectively; and the MTT assay was performed. Cell viability was calculated according to the following formula: cell viability (%)= (average value of absorption value of cells in experimental group/average value of absorption value of cells in control group)×100%. Final experimental data were obtained after averaging and standard deviation of the five parallel experimental data for each group. The experimental results are as shown in FIG. 9.

4. Breast Cancer Subcutaneous Tumor Detection Experiment of Nanoprobe

Figure 10:
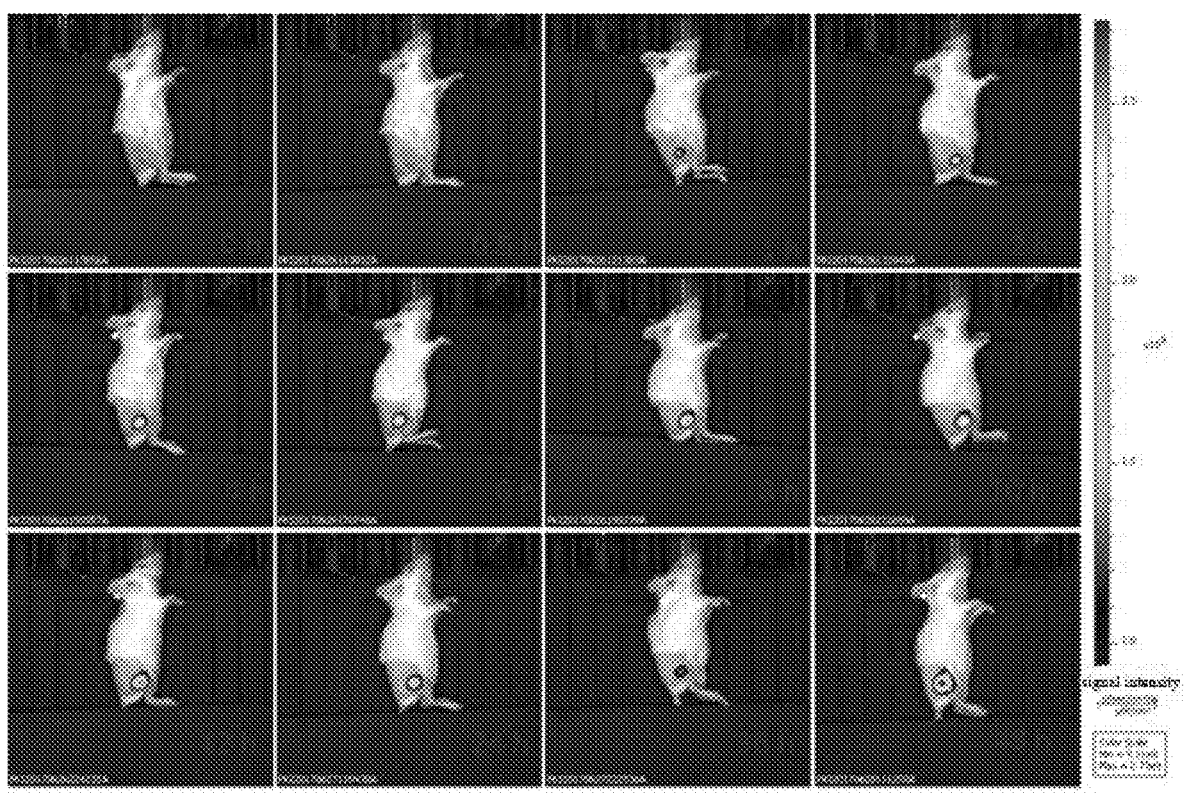
FIG. 10 is a subcutaneous tumor imaging experiment of a nanoprobe 4T1 provided by an experiment of the present invention.
Figure 11:
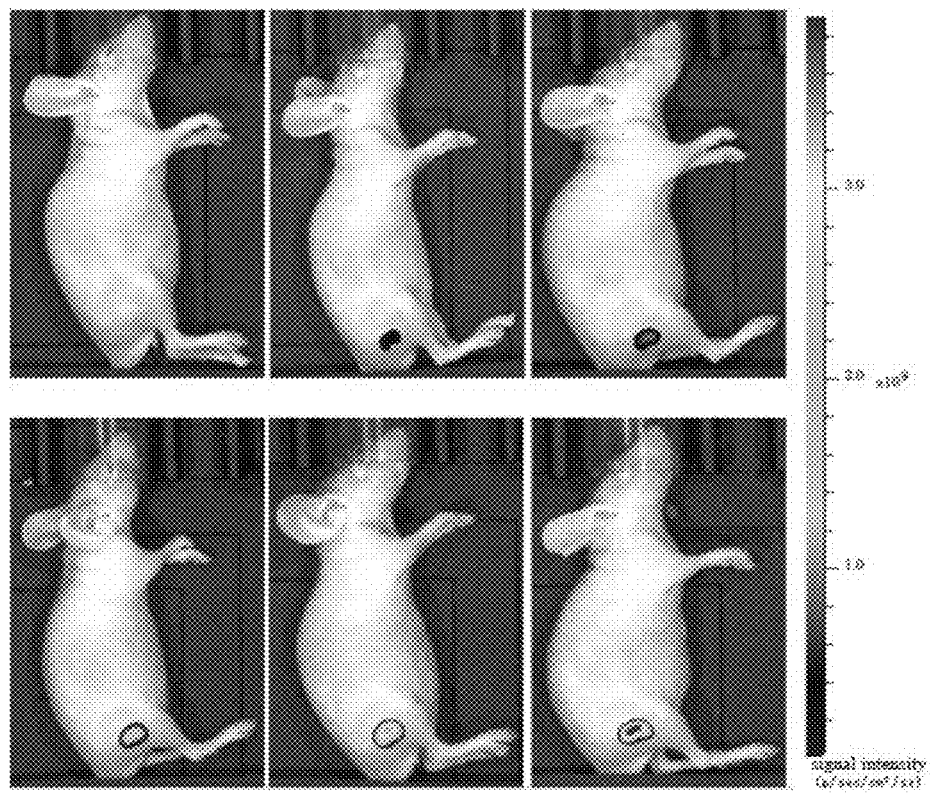
FIG. 11 is a diagram of subcutaneous tumor imaging experiment of a nanoprobe MCF7 provided by an experiment of the present invention.

Inoculating the cultured breast cancer cells MCF-7 and 4T1 ($1 \times 10^6$, 100 μL) into the hind limbs of female mice to construct a breast subcutaneous tumor model of the mouse. Measuring the tumor diameter and volume (tumor volume=$0.52 \times a \times b^2$, a and b are the long and short diameters of the tumor, respectively) to monitor the states of tumor growth and surface vessel growth. Anesthetizing the tumor-bearing nude mice with a gas, heating the tail vein with a heating pad, injecting 200 μL (1 mg·mL$^{-1}$) probe into the mice through the tail vein injection, and the fluorescence imaging was performed at different time points (0.5 h, 1 h, 3 h, 6 h, 8 h, 12 h, 24 h, 36 h, 48 h, 72 h, 96 h, 108 h) after injection. By detecting the fluorescence signals, the distribution of probes in vivo and their ability to target (passively) were further examined. As shown in FIGS. 10 and 11.

5. Glioma In Situ Detection Experiment of Nanoprobe

Healthy Babl/c mice, after anesthesia with isoflurane, the head of the mouse was fixed with a brain stereotaxic instrument, and the skin of the head was disinfected with iodophor. The scalp was cut through the median line and the skull was exposed. A cranial drill was used to drill out the bone window at 1.2 mm next to the midline and 1.2 mm by the crown line, a micro-syringe was fixed in the bone window, and pushing the needle downward for 1-2 mm to inoculate 10 μL $1 \times 10^6$·mL$^{-1}$ U87 cell fluid, leaving the needle for 5 min after injection, and suturing the scalp. The mice were cultured for 2 weeks to form tumors, and the in-situ glioma model of mice were constructed.

Figure 12:
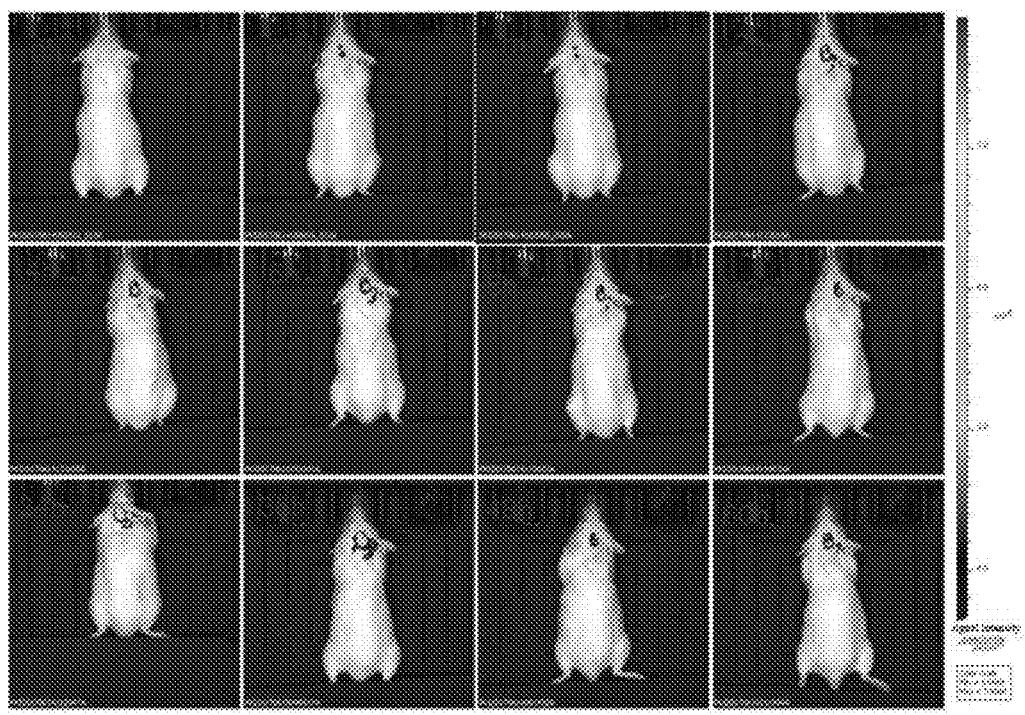
FIG. 12 is a diagram of brain tumor in situ imaging experiment of a nanoprobe provided by an experiment of the present invention.

Anesthetizing the tumor-bearing nude mice with a gas, heating the tail vein with a heating pad, injecting 200 μL (1 mg·mL$^{-1}$) probe into the mice through the tail vein injection, and the fluorescence imaging was performed at different time points (0.5 h, 1 h, 3 h, 6 h, 8 h, 12 h, 24 h, 36 h, 48 h) after injection. By detecting the fluorescence signals, the distribution of probes in vivo and their ability to target (passively) were further examined. As shown in FIG. 12.

6. The Detection Experiment of Lymph Node Metastasis in Glioma

Figure 13:
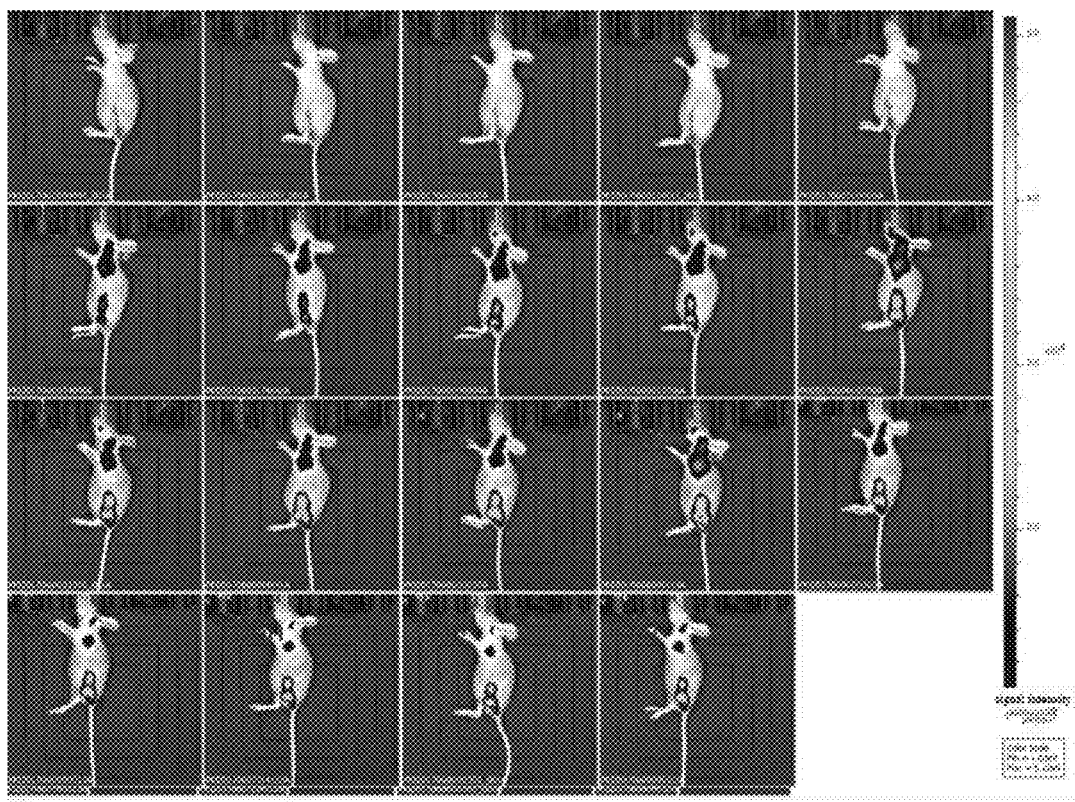
FIG. 13 is a diagram of lymph node metastasis tumor imaging experiment of a nanoprobe 4T1 provided by an experiment of the present invention.

Removing the lesions of the mice subcutaneously inoculated with breast cancer cell 4T1 in the embodiment 8, after 3 days of feeding, the postoperative nude mice were anesthetized with gas, the tail vein was heated with a heating pad, and 200 μL (1 mg·mL$^{-1}$) of probe was injected into the mice through the tail vein injection, and the fluorescence imaging was performed at different time points (0.5 h, 1 h, 3 h, 6 h, 8 h, 12 h, 24 h) after injection, and then observing the lymph node metastases. As shown in FIG. 13.

The foregoing descriptions are merely preferred embodiments of the present invention, which are not used to limit the present invention. Any modifications, equivalent substitutions, improvements within the spirit and principle of the present invention should be included in the protection scope of the present invention.

What is claimed is:

1. A pH-responsive ultrasensitive fluorescent nanoprobe, comprising a pH-responsive matrix material, a fluorescent organic small molecule dye, a first ligand and a second ligand;
   wherein the pH-responsive matrix material comprises calcium phosphate (CaP) and the fluorescent organic small molecule dye is a positively charged dye or a negatively charged dye;
   and a plurality of the fluorescent organic small molecule dyes are aggregated by a mutual electrostatic adsorption between the first ligand or the second ligand and the fluorescent organic small molecule dye,
   wherein the first ligand, the second ligand and the fluorescent organic small molecules form dye-coated nanoparticles,
   wherein the first ligand and the second ligand are independently selected from polyacrylic acid (PAA) or polyethylenimide (PEI),
   wherein the calcium phosphate is deposited on a surface of an aggregation of the first or second ligand and the fluorescent organic small molecule dye by adjusting a pH and adding phosphate for mineralization to form the pH-responsive ultrasensitive fluorescent nanoprobe.

2. The pH-responsive ultrasensitive fluorescent nanoprobe of claim 1, wherein the positively charged dye is IR780, RhB or IR800.

3. The pH-responsive ultrasensitive fluorescent nanoprobe of claim 1, wherein the negatively charged dye is Cy3, Cy5, Cy5.5, Cy7, ICG, ICG-Der-01, ICG-Der-02, ICG-Der-03, IR820, Alexa Fluor 750, Alexa Fluor 700, Alexa Fluor 680, Alexa Fluor 660, Alexa Fluor 647, Alexa Fluor 635, Alexa Fluor 633, Alexa Fluor 610, Alexa Fluor 594, Alexa Fluor 568, Alexa Fluor 555, Alexa Fluor 546, Alexa Fluor 532, Alexa Fluor 514, Alexa Fluor 500, Alexa Fluor 488, or FITC.

4. A preparation method of the pH-responsive ultrasensitive fluorescent nanoprobe of claim 1, wherein the preparation method comprises aggregating
the negatively charged dye with the PEI and the PAA to obtain a PEI/PAA nanosphere and coating the PEI/PAA nanosphere with the matrix material, wherein the negatively charged dye is enriched on a PEI molecular chain due to an absorption of the negatively charged dye by the PEI; meanwhile, a negatively charged PAA is added, and then the PEI absorbs both the negatively charged dye and the negatively charged PAA and is self-assembled into the PEI/PAA nanosphere; exposed carboxyl groups on the PEI/PAA nanosphere are coordinated with $Ca^{2+}$, and the calcium phosphate is deposited on a surface of the PEI/PAA nanosphere by adjusting the pH and adding the phosphate for mineralization to form the dye-coated nanoparticle.

5. The preparation method of the pH-responsive ultrasensitive fluorescent nanoprobe of claim 4, wherein the pH-responsive matrix material is the calcium phosphate (CaP); the positively charged dye is IR780, RhB, or IR800.

6. The preparation method of the pH-responsive ultrasensitive fluorescent nanoprobe of claim 4, wherein the pH-responsive matrix material is the calcium phosphate (CaP); the negatively charged dye is ICG, IR820, or a dye from Alexa Fluor series and Cy series.

7. A method for using the pH-responsive ultrasensitive fluorescent nanoprobe of claim 1, comprising the following steps:
the dye-coated nanoparticle is injected into a mouse via tail vein, reaches a tumor site through an EPR effect and is enriched in the tumor site, wherein the fluorescent organic small molecule dye in the dye-coated nanoparticle is IR780;

in normal tissues and blood, a pH is neutral or weakly alkaline, and the fluorescent organic small molecule dyes in the dye-coated nanoparticle are in a state of aggregation quenching;
in the tumor site, due to weak acidic conditions, the pH-responsive matrix material comprising the calcium phosphate (CaP) is dissolved and releases the fluorescent organic small molecule dyes, and the fluorescent organic small molecule dyes recover after the IR780 recovers to a free molecular state, thereby realizing fluorescence enhancement.

8. A CaP/IR780 probe prepared by the preparation method of claim 4, wherein the CaP/IR780 probe comprises the calcium phosphate (CaP) as the pH-responsive matrix material and the IR780 as the positively charged dye.

9. A CaP/ICG probe prepared by the preparation method of claim 4, wherein the CaP/ICG probe comprises the calcium phosphate (CaP) as the pH-responsive matrix material and the ICG as the negatively charged dye.

10. A CaP/IR780 prepared by the preparation method of claim 5, wherein the CaP/IR780 probe comprises the calcium phosphate (CaP) as the pH-responsive matrix material and the IR780 as the positively charged dye.

11. A CaP/ICG probe prepared by the preparation method of claim 6, wherein the CaP/ICG probe comprises the calcium phosphate (CaP) as the pH-responsive matrix material and the ICG as the negatively charged dye.

12. The pH-responsive ultrasensitive fluorescent nanoprobe of claim 1, wherein the fluorescent organic small molecule dyes are dyes with aggregation quenching effect;
the fluorescent organic small molecule dyes are fluorescence quenched due to being in an aggregation state;
the fluorescent organic small molecule dyes are fluorescence recovered due to being in a single molecule state.

* * * * *